United States Patent [19]

Vallette

[11] 4,307,021
[45] Dec. 22, 1981

[54] PROCESS FOR OBTAINING 1,5-DINITRO-ANTHRAQUINONE OF HIGH PURITY

[75] Inventor: Maurice R. J. Vallette, Precy-sur-Oise, France

[73] Assignee: Produits Chimiques Ugine Kuhlmann, Courbevoie, France

[21] Appl. No.: 52,883

[22] Filed: Jun. 28, 1979

[30] Foreign Application Priority Data

Jul. 27, 1978 [FR] France .................. 78 22215

[51] Int. Cl.² ......................................... C07C 76/00
[52] U.S. Cl. ................................................. 260/369
[58] Field of Search ........................................ 260/369

[56] References Cited

U.S. PATENT DOCUMENTS 4,042,604  8/1977  Eilingsfeld et al. ............... 260/369
4,053,488  10/1977  Bruehemann et al. ............ 260/369

Primary Examiner—Winston A. Douglas
Assistant Examiner—Raymond K. Covington
Attorney, Agent, or Firm—Beveridge, De Grandi, Kline & Lunsford

[57] ABSTRACT

The invention relates to a process for obtaining 1,5-dinitro-anthraquinone of high purity from crude mixtures of dinitro-anthraquinones. Said mixture is treated at a temperature ranging from 150° C. to 200° C. with an ester having a boiling point greater than 150° C. derived from an aliphatic alcohol containing 1 to 4 carbon atoms and a mono- or di-carboxylic acid or phosphoric acid, and then, after possible cooling without the temperature falling below 150° C., separating the insoluble material consisting essentially of 1,5-dinitro-anthraquinone.

9 Claims, No Drawings

PROCESS FOR OBTAINING 1,5-DINITRO-ANTHRAQUINONE OF HIGH PURITY

The present invention relates to a process for obtaining 1,5-dinitro-anthraquinone of high purity.

The dinitration of the anthraquinone may be effected in sulfuric acid by the action of nitric acid (J. Chem. Soc., 1920, 117, pp. 1001-1004; Hefti, Chem. Acta, 1931, 14, pp. 1404-1427; French Pat. No. 2,294,162 which corresponds to British Pat. No. 1,523,749 and French Pat. No. 2,151,965 which corresponds to U.S. Pat. No. 3,818,052) or in nitric acid (Boettger and Pettersen, Annalen, 1881, 166, p. 154 and German Patent Application Nos. 2,306,611 and 2,351,590 which correspond, respectively, to U.S. Pat. Nos. 3,906,011 and 3,963,762.

During this dinitration whatever may be the process used, there is formed, in addition to the 1,5-dinitro derivative, a considerable proportion of 1,8-dinitro derivative and of $\alpha,\beta$ derivatives (1,6 and 1,7 isomers) and $\beta,\beta'$ derivatives (2,6 and 2,7 isomers). The 1,5-dinitro-anthraquinone is an important intermediate product for the preparation of dyes for natural and synthetic fibers (Color Index Nos. 62,500, 64,500, 65,405, 65,415, 65,425, 69,015, 69,025 and 70,510). For this use, it is desirable to prepare a 1,5-dinitro-anthraquinone of high purity by separating it from the undesired isomers contained in the crude product resulting from the dinitration.

To effect this separation, various methods have hitherto been recommended.

(a) A method which comprises filtering after the nitration in order to take advantage of the solubility of the $\alpha,\beta$ and $\beta,\beta'$ derivatives in sulfuric acid (French Pat. Nos. 2,294,162 and 2,151,965), has the disadvantage of leading to a not negligible loss of $\alpha,\alpha'$ derivatives.

(b) Another method comprises treating the crude product in nitric acid (German Patent Applications Nos. 2,306,611 and 2,351,590) or in solvents such as nitrated aromatic hydrocarbons, for example nitrobenzene and nitrotoluene (French Pat. No. 2,155,660 which corresponds to U.S. Pat. No. 4,076,734), chlorinated aromatic hydrocarbons, nitriles and cyclic sulfones (French Pat. No. 2,307,792 which corresponds to U.S. Pat. No. 3,996,251), N-methyl-pyrrolidone alone or admixed with hydrocarbons, alcohols, ketones, ethers, or acids (French Pat. No. 2,327,227) or also in a mixture of concentrated nitric acid and a chlorinated aliphatic hydrocarbon (French Pat. No. 2,256,911 which corresponds to U.S. Pat. No. 4,045,455). However, this method has disadvantages either because the solvents used are difficult to recover, or because they do not allow a 1,5-dinitro-anthraquinone of high purity to be obtained.

It has now been found that a 1,5-dinitro-anthraquinone of high purity can be obtained from mixtures containing, in addition to the 1,5-dinitro-anthraquinone, up to 75% by weight of other dinitro derivatives and possibly of mononitro-anthraquinone and anthraquinone, when such a mixture is treated at a temperature of from 150° to 200° C. with an ester having a boiling point at atmospheric pressure greater than 150° C., preferably greater than 170° C., derived from an aliphatic alcohol containing 1 to 4 carbon atoms and a mono- or di-carboxylic acid or phosphoric acid, then, after eventual cooling without going below 150° C., the insoluble material consisting essentially of 1,5-dinitro-anthraquinone is separated by the usual methods, for example by filtration.

Examples of the ester to be used in the invention are methyl or ethyl benzoate, trimethyl or triethyl phosphate, and preferably dimethyl or diethyl phthalate. A mixture of these solvents may also be used.

The mixtures to be purified may come from the dinitration of anthraquinone or from the nitration of 1-nitro-anthraquinone by means of nitric acid, possibly in the presence of sulfuric acid. Mixtures obtained synthetically or mixtures already partly purified, for example mixtures of 1,5 and 1,8 isomers, can also be used.

The mixture of dinitro-anthraquinones may be introduced into the ester previously heated to the temperature selected for the treatment; the mixture of dinitro-anthraquinones may also be introduced into the cold ester, then heated to the desired temperature. It is evident that, unless working under pressure, this temperature must be below the boiling point of the ester used. The time of contact between the ester and the mixture to be purified may vary between 30 minutes and 15 hours.

In general, the quantity by weight of ester used is between 2 and 12 times, preferably between 3 and 8 times, that of the mixture of the dinitro-anthraquinones considered in the dry state.

Instead of starting from a dry mixture, a press cake coming from the nitration may be used directly. The water is then removed by distillation.

The ester remaining in the cake after filtration may be eliminated by washing with other solvents such as methanol, ethanol and tert. butanol.

The following examples, in which the parts and the percentages are by weight, illustrate the invention without it being limited thereto.

EXAMPLE 1

75 Parts of a mixture of dinitro-anthraquinone having the composition:

| | |
|---|---|
| 1,5-dinitro-anthraquinone | 41.7% |
| 1,8-dinitro-anthraquinone | 37.8% |
| 1,6 and 1,7-dinitro-anthraquinones | 17.5% |
| 2,6- and 2,7-dinitro-anthraquinones, 1-nitro-anthraquinone and anthraquinone | 3.0% | are contacted with stirring with 300 parts of dimethyl phthalate. The mixture is heated to 180° C. and this temperature is maintained for two hours, then the mixture is cooled to 170° C. and this temperature is maintained for 30 minutes. The product is then filtered on fritted glass preheated to 170° C., drained, and the cake washed with methanol and dried at about 60° C. until constant weight is obtained. 25.5 Parts of 1,5-dinitro-anthraquinone at 92.3% of purity are thus obtained, i.e. a theoretical yield of 75.25%.

EXAMPLE 2

The operation is as in Example 1, but the mixture is maintained at 180° C. for 6 hours. 24.8 Parts of 1,5-dinitro-anthraquinone at 94.7% of purity are obtained, that is, a theoretical yeild of 75.1%.

EXAMPLE 3

The operation is as in Example 1, but the temperature is maintained at 180° C. for 15 hours. 26.1 Parts of 1,5- dinitro-anthraquinone at 93.4% of purity are obtained, that is a theoretical yield of 77.8%.

EXAMPLE 4

The operation is as in Example 1, but 600 parts of dimethyl phthalate are used. 20.7 Parts of 1,5-dinitro-anthraquinone at 96.6% of purity are obtained, that is a theoretical yeild of 63.9%.

EXAMPLE 5

The operation is as in Example 1, but before washing the cake with methanol, it is treated again under the same conditions (2 hours at 180° C., then 30 minutes at 170° C.) with 300 parts of dimethyl phthalate. 22.1 Parts of 1,5-dinitro-anthraquinone at 97.8% of purity are then obtained, that is, a theoretical yield of 69%.

In the following Table are collected the results obtained on operating as in Example 1, but starting from mixtures of dinitro-anthraquinones having the composition indicated.

TABLE

|  | Ex. 6 | Ex. 7 | Ex. 8 | Ex. 9 | Ex. 10 |
|---|---|---|---|---|---|
| COMPOSITION OF THE MIXTURE OF DINITRO-ANTHRAQUINONES (%) | | | | | |
| 1,5-dinitro-anthraquinone | 51.6 | 72.1 | 85.8 | 54.5 | 27.4 |
| 1,8-dinitro-anthraquinone | 39.6 | 27.9 | 13.1 | 45 | 20.8 |
| 1,6- and 1,7-dinitro-anthraquinones | 8.3 | — | 1.1 | 0.5 | 49 |
| 2,6- and 2,7-dinitro-anthraquinones | 0.5 | — | | | 2.8 |
| RESULTS | | | | | |
| Weight of 1,5-dinitro-anthraquinone obtained (in parts) | 35.9 | 49.6 | 61 | 37.1 | 11.4 |
| Purity (%) | 94.3 | 93.9 | 97.1 | 94.2 | 96.2 |
| Theoretical yield (%) | 87.4 | 86.25 | 92 | 85.4 | 53.3 |

EXAMPLE 11

The operation is as in Example 1, but the dimethyl phthalate is replaced by 450 parts of diethyl phthalate. 27.2 Parts of 1,5-dinitro-anthraquinone at 91.4% purity are obtained, that is a theoretical yield of 79.4%.

EXAMPLE 12

The operation is as in Example 1, but the dimethyl phthalate is replaced by 600 parts of diethyl phthalate. 25 Parts of 1,5-dinitro-anthraquinone at 94.1% purity are obtained, that is a theoretical yield of 75%.

EXAMPLE 13

The operation is as in Example 1, but the dimethyl phthalate is replaced by trimethyl phosphate and a mixture of dinitro-anthraquinones having the following composition is used:

| 1,5-dinitro-anthraquinone | 51.6% |
|---|---|
| 1,8-dinito-anthraquinone | 39.6% |
| 1,6- and 1,7-dinitro-anthraquinones | 8.3% |
| 2,7-dinitro-anthraquinone | 0.5% |

34.4 Parts of 1,5-dinitro-anthraquinone having a plurality of 92.4% are obtained, that is a theoretical yield of 82%.

EXAMPLE 14

The operation is as in Example 1, but the dimethyl phthalate is replaced by trimethyl phosphate and a mixture of dinitro-anthraquinones having the following composition is used:

| 1,5-dintro-anthraquinone | 92% |
|---|---|
| 1,8-dinitro-anthraquinone | 6% |
| 1,6- and 1,7-dinitro-anthraquinones | 2% |

66.2 Parts of 1,5-dinitro-anthraquinone of 96% purity are obtained, i.e. a theoretical yield of 92%.

EXAMPLE 15

The operation is as in Example 5, but methyl benzoate is used instead of dimethyl phthalate. 23 Parts of 1,5-dinitro-anthraquinone of 97.2% purity are obtained, that is a theoretical yield of 71.7%.

EXAMPLE 16

The operation is as in Example 5, but ethyl benzoate is used instead of dimethyl phthalate. 27 Parts of 1,5-dinitro-anthraquinone of 93% purity are obtained, that is a theoretical yield of 80%.

EXAMPLE 17

305 Parts of dimethyl phthalate are mixed with stirring with 260 parts of a press cake provided from the dinitration of anthraquinone and containing 75 parts of a mixture of dinitro-anthraquinones having the same composition as in Example 1. By heating to 180° C. and maintaining this temperature for two hours, the water (185 parts) is eliminated by distillation at the same time as 5 parts of dimethyl phthalate. The product is then allowed to cool to 170° C., maintained at this temperature for 30 minutes and the process is completed as in Example 1.

24 Parts of 1,5-dinitro-anthraquinone of 93.1% purity are obtained, that is a theoretical yield of 71.4%.

What is claimed is:

1. A process for obtaining 1,5-dinitro-anthraquinone of high purity from a mixture containing in addition to the 1,5-dinitro-anthraquinone, up to 75% by weight of a member selected from the group consisting of other dinitro derivatives and mixtures thereof with mononitro-anthraquinone and anthraquinone, which comprises treating said mixture at a temperature ranging from 150° C. to 200° C. with an ester having a boiling point at atmospheric pressure greater than 150° C. derived from an aliphatic alcohol containing 1 to 4 carbon atoms and a mono- or di-carboxylic acid or phosphoric acid, and then, after possible cooling without the temperature falling below 150° C., separating the insoluble material consisting essentially of 1,5-dinitro-anthraquinone.

2. The process according to claim 1 in which the ester is methyl benzoate, ethyl benzoate, trimethyl phosphate, triethyl phosphate, dimethyl phthalate, diethyl phthalate or a mixture of these compounds.

3. The process according to claims 1 or 2 in which the ester is used in a quantity by weight between 2 and 12 times, preferably between 3 and 8 times, that of the dry weight of the mixture of dinitro-anthraquinones.

4. The process according to claim 3 in which the mixture of dinitro-anthraquinones is in the form of a press cake and the water therein is eliminated by distillation.

5. The process according to claims 1 or 2 in which the mixture of dinitro-anthraquinones is in the form of a press cake and the water therein is eliminated by distillation.

6. The process according to claim 5 in which the time of treatment varies between 30 minutes and 15 hours.

7. The process according to claim 4 in which the time of treatment varies between 30 minutes and 15 hours.

8. The process according to claim 3 in which the time of treatment varies between 30 minutes and 15 hours.

9. The process according to claims 1 or 2 in which the time of treatment varies between 30 minutes and 15 hours.

* * * * *